United States Patent [19]
Lett et al.

[11] Patent Number: 5,298,250
[45] Date of Patent: Mar. 29, 1994

[54] INSECT REPELLENT

[75] Inventors: Bryan D. Lett, Bilgola Plateau; Harold S. Kraus, Dural, both of Australia

[73] Assignee: R & C Products Pty Ltd., Ermington, Australia

[21] Appl. No.: 983,572

[22] PCT Filed: Aug. 5, 1991

[86] PCT No.: PCT/AU91/00343

§ 371 Date: Feb. 5, 1993

§ 102(e) Date: Feb. 5, 1993

[87] PCT Pub. No.: WO92/02136

PCT Pub. Date: Feb. 20, 1992

[30] Foreign Application Priority Data

Aug. 6, 1990 [AU] Australia .................. PK 1581

[51] Int. Cl.$^5$ ........................... A01N 31/06
[52] U.S. Cl. .................. 424/405; 424/45; 424/DIG. 10; 514/919
[58] Field of Search ......... 424/45, 405, DIG. 10; 514/919

[56] References Cited

U.S. PATENT DOCUMENTS

| | | | |
|---|---|---|---|
| 4,237,072 | 12/1980 | Aviron-Violet et al. | 568/459 |
| 4,774,082 | 9/1988 | Flashinski | 514/919 |
| 5,017,377 | 5/1991 | Sikinami et al. | 424/409 |
| 5,130,136 | 7/1992 | Shono et al. | |

FOREIGN PATENT DOCUMENTS

| | | | |
|---|---|---|---|
| 89B43901 | 5/1990 | Australia | A01N 31/60 |
| 60-199804 | 10/1985 | Japan | A01N 47/18 |
| 3-133906 | 6/1991 | Japan | A01N 41/04 |
| 3-176404 | 7/1991 | Japan | A01N 37/08 |
| 8906904A | 8/1989 | PCT Int'l Appl. | A01N 65/00 |

OTHER PUBLICATIONS

Nishimura et al., "Allelopathic Substances, p-Menthane-3,8-diols Isolated ...", *Agric. Biol. Chem.* 46, 319-20 (1982).

Zimmerman et al., "Stereoisomerism of Isopulegol Hydrates and Some ...", *J. Am. Chem. Soc.*, 75, 2367-70 (1953).

Stoll et al., "Produits Secondaires de la Préparation de ...", *Helv. Chim. Acta* 31, 1-4 (1948) + Translation.

Clark et al., "Acid-Catalyzed Cyclization of Terpenoids in a Micellar System ...", *J. Org. Chem.* 49, 4557-9 (1984).

*Primary Examiner*—Thurman K. Page
*Assistant Examiner*—Robert H. Harrison

[57] ABSTRACT

An insect-repellent composition is disclosed which includes an insect repellent such as p-menthane-3,8-diol and a synergistic amount of an acetal of formula (Z). A method of forming a preferred composition is also disclosed in which citronellal undergoes an acid-cyclization reaction to yield an impure mixture of p-menthane-3,8-diols and acetals. The impure mixture is subjected to fractional distillation to remove a low boiling point fraction and to thereby yield a remaining fraction which constitutes the preferred composition.

13 Claims, 1 Drawing Sheet

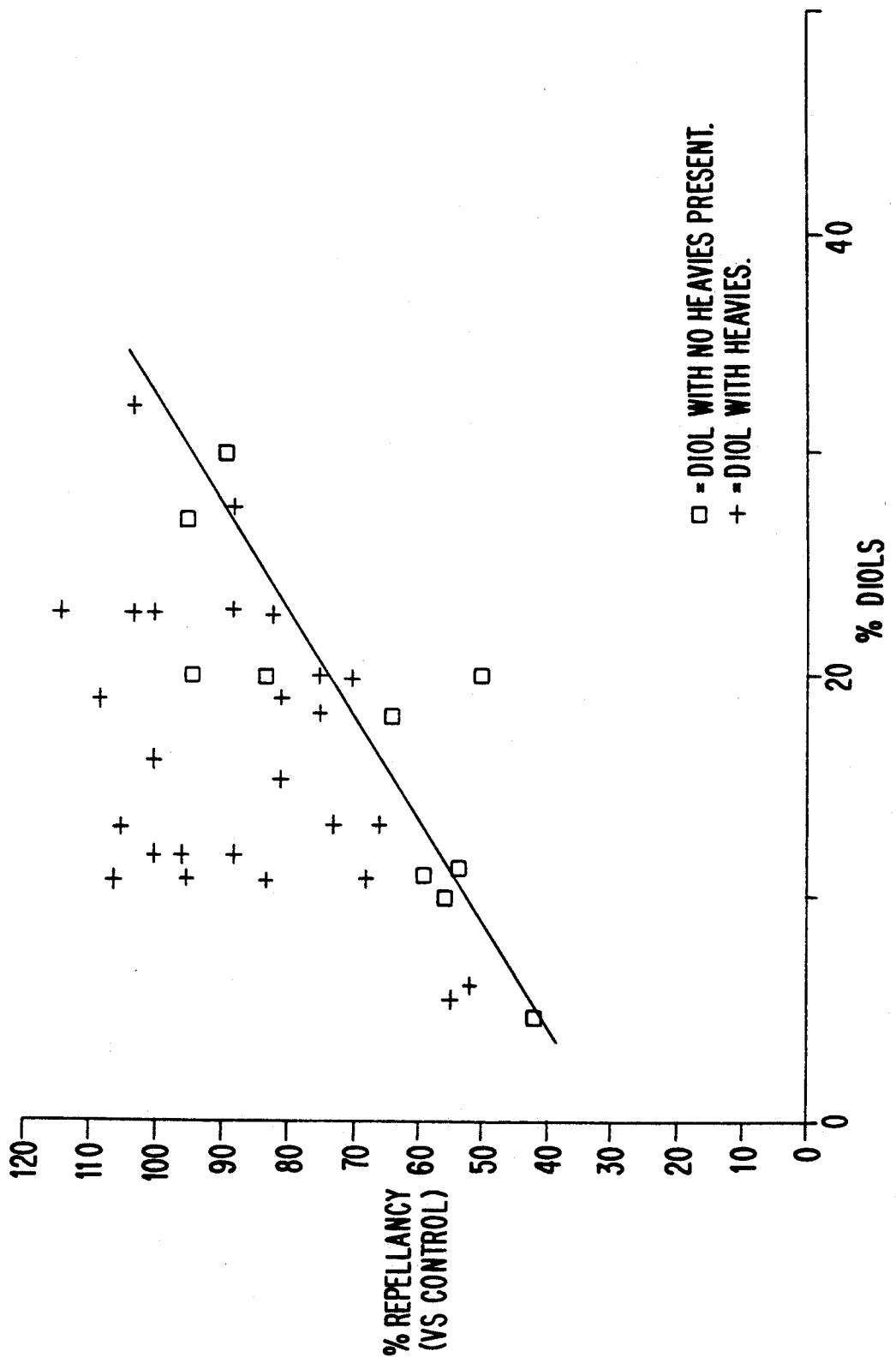

INSECT REPELLENT

FIELD OF THE INVENTION

This invention relates to synergistic insect repellent compositions, in particular compositions based on insect repellents such as p-menthane-3,8-diols and as synergist acetals, particularly those resulting from the acid catalysed cyclization of citronellal.

BACKGROUND ART

Compositions that repel insects, particularly insect pests such as mosquitoes, flies and fleas, are widely used to prevent animals from being bitten by such insects. The importance of preventing biting is essentially two-fold. Firstly, there are a number of insects which are capable of infecting animals with disease causing parasites, an example being the transmission of Plasmodium by mosquitoes to cause malaria. Secondly, in many cases whether disease is transmitted or not, the bite can be extremely irritating.

Of course, man is one animal that suffers from biting insects. Man also suffers irritation from non-biting, annoying insects such as domestic flies and from insects that transmit disease by contact.

The prior art discloses many compositions having repellency to some or a number of insect species. Of these compositions, the most widely used includes the active ingredient N,N-diethyl-m-toluamide (DEET).

Generally, compositions based on DEET are in the form of lotions or aerosols to be applied or sprayed onto the exposed skin. Such compositions may include a variety of other ingredients such as film forming agents to enhance substantivity to the skin and potentiators such as those disclosed in WO89/06904-A.

Although DEET containing compositions are relatively effective particularly in repelling domestic flies and mosquitoes, concerns have been expressed about its toxicity to humans.

Other compositions that are known repellents include various extracts of naturally occurring compounds obtained from eucalyptus species. One series of naturally occurring compounds obtained from Eucalyptus citriodora are the p-menthane-3,8-diols. These compounds are known to exert a repellent effect on insect pests such as mosquitoes and fleas.

Thus in Nishimura et al. Agric. Biol. Chem. 46(1) 319 (1982), the authors disclose the isolation of cis and trans p-menthane-3,8-diols in the form of racemic mixtures from Eucalyptus citriodora. In addition (+) and (−) cis and (+) and (−) trans isomers were synthesized. All compounds were tested for their effectiveness as plant growth regulators but no mention is made of any insect repellent properties.

In an earlier publication, J. Am. Chem. Soc. 75, 2367 (1953), Zimmerman and English report the synthesis of the cis and trans p-menthane-3,8-diols, designated Va and Vb respectively, through the acid cyclization of citronellal. Again no mention is made of any insect repellent properties.

In JP60-199804-A (Nippon Kayaku KK), it is disclosed that the cis and trans p-menthane-3,8-diols are effective insect repellents, as are a number of analogues. This patent application teaches that the p-menthane-3,8-diols may be prepared using the method disclosed in J. Am. Chem. Soc. 75, 2367 (1953). Using (+)-citronellal as the starting material and a reaction time of 27 hours at room temperature cis:trans p-menthane-3,8-diols in a ratio of 5:2 are obtained. These compounds are obtained in pure form following chromatographic separation and recrystallization. There is no mention of the use of the so-purified p-menthane-3,8-diols with any other insect repellent.

EP 367140-A (Takiron Co. Ltd) also relates to the use of p-menthane-3,8-diols as insect repellents. This application teaches slow-release compositions wherein the diols are included in compositions with an ethylene/vinyl acetate copolymer.

Although the p-menthane-3,8-diols are effective insect repellents, even the most efficient routes of synthesis currently known results in products that are so costly that repellent compositions including these menthanediols are too expensive compared with known alternatives.

However, in view of the effectiveness of the menthanediols, considerable effort has been put into developing more cost efficient routes of synthesis.

To that end the present applicants in investigating more efficient routes of synthesis pursued a synthetic route in which the starting material, citronellal, was subjected to acid catalysed cyclization (Prins reaction). This reaction causes the cyclization of the citronellal to produce an impure mixture of 40-45% cis and trans p-menthane-3,8-diols and is essentially the method disclosed in J. Am. Chem. Soc. 75, 2367 (1953). This impure mixture also includes unreacted citronellal, compounds having a boiling point about the same as or lower than citronellal and high boiling point compounds.

As it has been found that the cis isomer is more active than the trans isomer, the cis isomer may be isolated from the above mixture and used in its pure form. For the purposes of comparison, the cost of the impure mixture is significantly lower than that of cis isomer of 99% purity.

SUMMARY OF THE INVENTION

Because of the relatively low cost of the aforementioned impure mixture, the present applicants evaluated the insect repellency of the mixture. It was found to be unsatisfactory. It was, however, found that when the compounds of boiling point about the same as citronellal or below were removed from the impure mixture, the resultant composition possessed an exceptionally high level of repellency. In fact the level of repellency observed was somewhat greater than would have been expected in view of the increased concentration of the p-menthane-3,8-diols.

The present invention therefore provides an insect-repellent composition comprising one or more insect repellents of the formula X:

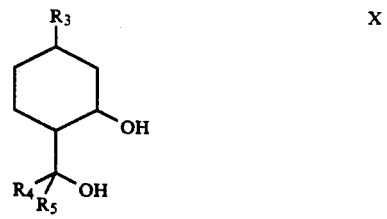

wherein $R_3$ is hydrogen or an alkyl group containing 1-4 carbon atoms; and $R_4$ and $R_5$ are the same or different and are alkyl groups containing 1-4 carbon atoms;

and a synergistic amount of at least one compound of the formula Z:

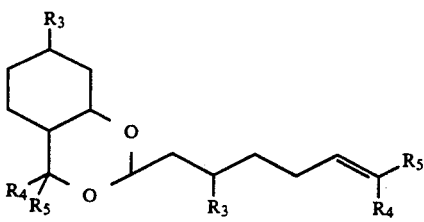

Z wherein $R_3$, $R_4$ and $R_5$ are as defined above, characterized in that the composition is substantially free of insect repellents having a boiling point less than about 80° C. at a pressure of 4 mm Hg.

Such a composition may be prepared by the acid catalysed cyclization of the citronellal derivative

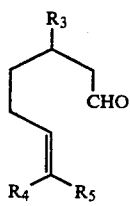

followed by partial purification of the reaction mixture. The diol X results from the reaction of the protonated starting material with water. Alternatively, the diol X may reversibly react with further starting material under the acid-catalysed conditions to give the bicyclic acetal Z.

DISCLOSURE OF THE INVENTION

The present inventors have found that it is a group of high molecular weight compounds of boiling point substantially higher than the p-menthane-3,8-diols that are synergistic with the p-menthane-3,8-diols. This high molecular weight group includes two main components which are acetals, of the formula C and D:

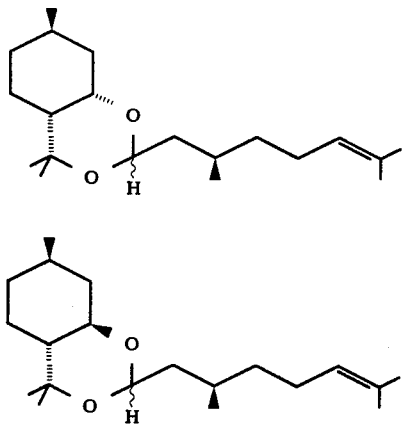

C

D

Each of these components comprises a mixture of two diastereoisomeric compounds, epimeric at the acetal carbon. It is to be understood that relative stereochemistry only is depicted in the structures; no limitation as to absolute configuration is intended, and the enantiomers of the structures depicted also fall within the scope of the invention.

It is believed that by removing the unreacted citronellal and other low boiling point compounds, synergism between the p-menthane-3,8-diols and these acetals was able to be observed as the low boiling point compounds did not interfere by displacing the p-menthane-3,8-diols and/or acetals from the repellent air layer formed immediately above the skin. Displacement occurs owing to the greater volatility of the low boiling point compounds. This explanation is entirely theoretical and it may well be that repellency of the synergistic mixture occurs as a result of an entirely different mechanism. In particular, it should be noted that citronellal is in itself a repellent, though its effectiveness is relatively low and short-lived. One might therefore expect that a mixture of citronellal and p-menthane-3,8-diols would have an enhanced repellency but this was found not to be the case. This suggests that citronellal acts as an antagonist in these compositions.

These acetals are known compounds being disclosed by Stoll and Bolle, Helv. Chim. Acta, 31, 1 (1948). This paper discloses on page 1, a compound (II) being an acetal that may be formed by the acid hydrolysis of the bisulphite addition compound of citronellal. On page 4, the synthesis of acetal (II) is described where the compound is found to have a boiling point of 127°–130° C. at 0.03 mm Hg. However, there is no hint or suggestion in this paper as to any utility of this acetal. It must also be realized that the authors did not isolate one pair of diastereoisomers from the other and in fact did not even acknowledge the existence of more than one diastereoisomer. Accordingly, components C and D mentioned above, having only now been isolated, are novel over the disclosure of this paper.

It should be further noted that none of the aforementioned disclosures, Agric. Biol. Chem. 46 (1) 319 (1982), J. Am. Chem. Soc. 75, 2367 (1953), JP60-199804-A or EP367140-A teach or suggest the combination of these acetals with the p-menthane-3,8-diols. Those references, in using the acid cyclization of citronellal to form the p-menthane-3,8-diols, could inherently include these acetals in combination with the diols on completion of the cyclization reaction. However, the completed reaction mixtures will also include unreacted citronellal and, as taught above, this compound must be removed in order to obtain the synergism between the p-menthane-3,8-diols and the acetals.

In this regard it should be particularly noted that in JP60-199804-A, the cis and trans p-menthane-3,8-diols are isolated and purified in a manner such that, if acetals were present in the reaction mixture, the so-obtained purified diols would be acetal-free.

Similarly, Clark et al., J. Org. Chem. 49 4557 (1984) in studying reaction rate enhancement and stereochemical course of reaction of the acid catalysed cyclization of citronellal to form cis and trans p-menthane-3,8-diols identify two isomeric isopulegols as reaction products, but no others.

The p-menthane-3,8-diols fall within the scope of compounds of the formula X when $R_3$, $R_4$ and $R_5$ are methyl groups, and are preferred insect repellents of the present invention. p-Menthane-3,8-diol is 2-hydroxy-a, a,4-trimethylcyclohexanemethanol and has four possible diastereoisomers, all of them pairs of enantiomers, arising from the three chiral centres at the 1, 2 and 4 carbon atoms. These may be denoted (1a, 2a, 4a)-, (1a, 2a, 4b)-, (1a, 2b, 4a)- and (1a, 2b, 4b)-, although the applicants are not aware of the first of these having been synthesized. The diastereoisomers most commonly used as insect repellents are the (1a, 2a, 4b)- form, commonly referred to as cis-p-menthane-3,8-diol, and the (1a, 2b, 4b)- form, commonly referred to as trans-p-menthane-3,8-diol, shown respectively in formulae A and B:

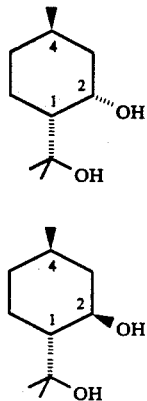

A

B

These are the two diastereomers that are generally formed from the acid cyclisation of citronellal—see J. Org. Chem. 49, 4457 (1984). The absolution configuration of the diols will depend upon whether the (+) or (−) enantiomers of citronellal are used or the racemic mixture (±)-citronellal.

All of the stereoisomers of the p-menthane-3,8-diols are within the scope of the present invention, particularly those arising from the acid cyclization of the (+) isomer and the racemic mixture. Mixtures of the cis and trans p-menthane-3,8-diols are particularly preferred, generally in a weight ratio of 2.5:1 to 1.4:1.

The compounds of the formula Z are acetals, preferably with either or all of the groups $R_3$, $R_4$, $R_5$ methyl. Most preferably a compound of the formula Z is:

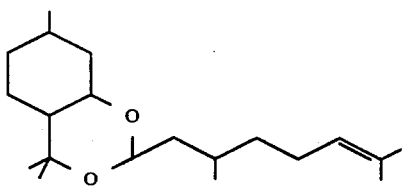

Preparation of this by the acid cyclization of racemic citronellal will give the various diastereoisomers of formula E:

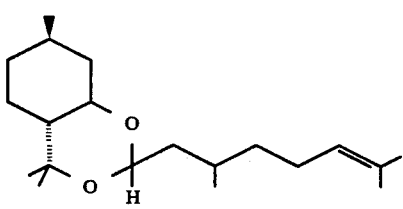

E

Particularly preferred compounds of the formula Z comprise the two diastereoisomers of formula C and D:

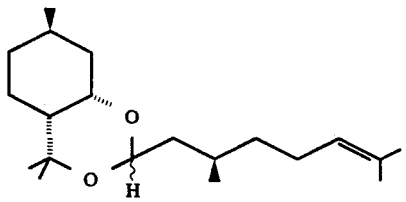

C

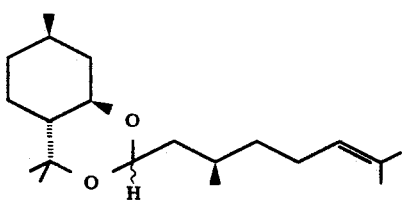

D or the enantiomers thereof.

The components C and D may be included individually in the compositions of the invention, preferably as a mixture. When used as a mixture in a composition including p-menthane-3,8-diols, a particularly desirable method for forming such compositions is to acid cyclize citronellal. The products of such a reaction will include the diols and acetals of formulae C and D. Conveniently, the unreacted citronellal and other low boiling compounds may be removed by fractional distillation to give a synergized insect repellent composition that can then be used as a base to form a variety of insect repellent products. Such products include personal use products such as aerosols, lotions, gels, roll-ons, pumps and sticks; foggers and bombs; vaporizers and ministrips for use for example in repelling moths from clothing; aerosols, pumps and powders for use on animals including domestic pets; and electrically operated vaporizers.

Preferably, fractional distillation will be conducted such that compounds of boiling point less than about 80° C. at 4 mm Hg, most preferably less than about 100° C. at 4 mm Hg will be removed.

The synergized compositions of the invention will generally include the insect repellent of formula X or Y and compound of the formula Z in a weight ratio of from 99:1 to 1:99. A preferred range is 38:1 to 1:19, most preferably 19:1 to 1.6:1. A particularly preferred ratio is 3.5:1 to 1.3:1.

When a composition includes compounds of the formula C and D and the mixture of cis-p-menthane-3,8-diol and trans-p-menthane-3,8-diol, it is preferred that they are included in concentrations of 20–40% w/w and 57–63% w/w respectively, with the diols in a weight ratio of 1.6:1 to 1.4:1.

MODES FOR CARRYING OUT THE INVENTION

In order to better understand the nature of the invention, a series of tests was conducted using a number of compositions of varying cis and trans p-menthane-3,8-diol content in the presence and absence of acetals of formula C and D. These tests sought to evaluate repellency against mosquitoes and domestic flies.

A typical test protocol used to determine repellency, in this case against flies, was as follows:

Target Insect

Housefly Musca domestica

Due to the erratic appearance of the various nuisance flies in the field, caged houseflies were used in the trial. The flies were bred in the insectary of Agrisearch Services Pty Ltd, at Orange, New South Wales, Australia. Breeding populations were originally collected from natural populations in the central west of New South Wales. Similar reactions to repellents have been found with the housefly and the other nuisance fly, the bushfly Musca vetustissima.

Treatment Method 0.7 gram of the lotions was weighed onto small pieces of plastic and then rubbed evenly over one forearm of the volunteer. The treatment area was from the elbow to the knuckles. The other arm was left untreated. Each treatment was replicated four times. One female and three males were the test subjects. For each replicate, the volunteers were treated with a different formulation.

Test Cages and Number of Flies

Nine wire cages each 25 cm×25 cm×40 cm, with cotton cheese cloth covers and a plastic window were used as the testing assemblies. Approximately 150 mixed adult 4–8 day old flies were released into each cage at the start of each replicate. Sufficient numbers of flies were present so that fly landings on the untreated arm were approximately 100 over a 60 second assessment.

Assessments

Assessments were made 1, 2, 3, 4, 5 and 6 hours after the treatments were applied. At each time the treated arm was introduced into a cage and the number of direct fly landings counted from the elbow to the knuckles over a 60 second period. Each cage was disturbed every 5 to 10 seconds and then the arm kept still as the count was made. The total of the 60 second count was recorded and then the untreated arm introduced into the cage and similar counts carried out. To allow for any bias that could occur in the order that arms were introduced, the whole process was repeated in an adjoining cage with the untreated arm introduced first.

% Repellencies were calculated using the following formula:

$$\% R = \frac{(C - T)}{C} \times 100$$

C=Number of flies landing on untreated arm
T=Number of flies landing on treated arm In each test, lotion type formulations were tested with a range of concentrations of cis and trans p-menthane-3,8-diols and acetals of formulae C and D.

BRIEF DESCRIPTION OF THE DRAWINGS

FIG. 1 is a graph of % repellency versus control achieved against mosquitoes of the species Aedes aegypti with varying levels of compositions including cis and trans p-menthane-3,8-diols with and without acetals of formulae C and D. These acetals are referred to on the graph as "heavies".

In FIG. 1 there is shown a graph of the results obtained against mosquitoes. From this it is evident that the only compositions of 100% or greater repellency versus control were those that included the acetals. Furthermore, generally compositions including the acetals had greater repellency than those without but having the same menthanediol content. This is particularly evident at about the 10% menthanediol level, where repellency versus control of about 105% was obtained with 6% acetal content.

For the sake of clarity, some of the specific acetal containing compositions repellency results are shown below in Table I.

TABLE I

| % Repellency versus control | Acetal Content (% w/w) | Diol Content (% w/w) |
|---|---|---|
| 52 | 9.75 | 6.0 |
| 106 | 6.0 | 10.8 |
| 100 | 13.0 | 11.9 |
| 105 | 8.25 | 13.4 |
| 100 | 10.0 | 16.2 |
| 114, 100 | 0.6 | 22.7 |
| 103 | 1.3 | 22.7 |
| 103 | 1.1 | 32.1 |

The results shown in FIG. 1 clearly indicate the synergistic nature of the combination of the cis and trans p-menthane-3,8-diols and the acetals of formula C and D, when used for repelling mosquitoes. Thus, it will be seen that the line on the graph indicates a clear trend of increasing repellency with increasing concentration of diols alone. On the other hand, substantially all of the repellency results for the menthanediol and acetal combination are above this trend line.

It should be noted that when the acetals were tested alone, they were found to be substantially non-repellent.

In a further series of tests, pairs of formulations, one of the pair having a relatively high concentration of menthanediol and a low concentration of acetals C and D and the other of the pair having a relatively low concentration of menthanediol and a relatively high concentration of acetals C and D, were tested for repellency against mosquitoes and flies. Each formulation was in the form of a lotion. These lotion formulations were as follows:

| Ingredient | FORMULA % w/w | | | | | |
|---|---|---|---|---|---|---|
| | A', B' | C' | D' | E', F' | G' | H' |
| Glycerol | 10 | — | — | — | — | — |
| Denatured absolute ethanol | 52 | 40 | 35 | 53.4 | 40 | 38.5 |
| Water | 14 | 36.2 | 31.4 | 20.0 | 36.4 | 30.2 |
| Crodolan AWS | 2.4 | 2.0 | 2.0 | — | 2.0 | — |
| Carbopol 940 | 0.8 | 0.6 | 0.6 | 0.8 | 0.6 | 0.6 |
| Teric 16M15 | 0.8 | 1.0 | 1.0 | 0.8 | 1.0 | 0.7 |
| Active | See Table II | | | | | |

Crodolan is a trade mark of Croda Chemicals
Carbopol is a trade mark of B.F. Goodrich & Co.
Teric is a trade mark of I.C.I.

The results of these tests are shown in Table II.

TABLE II

| EXHIBIT | FORMULA | % COMPOSITION P-menthane-3,8-diols | | | REPELLANCY (% of control) | |
|---|---|---|---|---|---|---|
| | | CIS | TRANS | ACETALS | MOSQUITO | FLIES |
| 1 | A' | 18 | 1 | 1 | 120 | 107 |
| | B' | 7.4 | 3.4 | 6 | 106 | 111 |
| 2 | C' | 18 | 1 | 1 | 75 | 103 |
| | D' | 11.1 | 5.1 | 10 | 100 | 113 |
| 3 | E' | 15 | 7.75 | 0.6 | 100 | 96 |
| | F' | 8 | 5.25 | 8.25 | 105 | 95 |
| 4 | G' | 1 | 18 | 1 | 50 | 83 |
| | H' | 1.5 | 16.8 | 7.8 | 75 | 106 |

Noticing that inherently the repellency results are most likely only accurate to ±5%, it is evident that the level of repellency can be maintained even when the menthanediol concentration is lowered, by increasing the level of acetals. This finding is important in that given a level of acceptable repellency, a lower level of menthanediol may be used in conjunction with sufficient of the acetals to maintain repellency.

Alternatively, if an enhanced level of repellency is required, menthanediol concentration can be maintained with an increased level of acetals being used to achieve the higher repellency.

In the former case, it is evident that a lower cost effective composition may be produced. In the latter case, a composition of greater activity may be produced at a lower cost than would otherwise be possible.

As previously mentioned a convenient method for forming preferred synergistic insect repellent compositions of the invention is to subject citronellal to acid catalysed cyclization. Specifically, these compositions have been formed as follows:

1. 4 kg citronellal is reacted with 20 kg of 5% sulphuric acid for a period of at least 5 hours, preferably 24 hours. The mixture is stirred throughout the reaction which is conducted under ambient conditions at a temperature not less than 10° C.
2. At the completion of the reaction, the mixture contains about 15-20% low boiling materials, including citronellal about 50-60% p-menthane-3,8-diols and about 20% acetals.
3. The organic phase of the reaction mixture is extracted with toluene, washed with water then 2% bicarbonate solution.
4. The washed organic phase is then subjected to fractional distillation at 4 mm Hg. Distillation results in the recovery of the toluene for further use and a fraction boiling at about 60°C.-100° C. The citronellal is within the latter fraction and may be reused in this form.
5. The fraction remaining, which boils at greater than about 100° C., includes cis and trans p-menthane-3,8-diols and the acetals C and D.

The citronellal starting material can be substantially pure (+), (−) or (±), or may be a Eucalyptus citriodora oil containing about 85% citronellal.

Compositions suitable for applications to the human skin may be readily produced by those skilled in the art. Such compositions include particularly aerosol and lotion forms, which may contain 5-50% w/w of the composition of the invention.

Examples of the compositions are as follows:

| Ingredient | % w/w |
|---|---|
| Lotion | |
| *Active | 30 |
| Emulsifiers | 5 |
| Fatty alcohol | 2 |
| Preservatives | 0.3 |
| Perfume | 0.6 |
| Thickener | 1.0 |
| Water | 61.1 |
| | 100.0 |
| Aerosol | |
| *Active | 30 |
| Isopropyl myristate | 5 |
| Ethanol | 34.5 |
| Perfume | 0.5 |
| Propellant | 30.0 |
| | 100.0 |

*Active: formed according to the method described above. Would typically contain 65 ± 8% w/w of cis and trans p-menthane-3,8-diols in a weight ratio of about 1.4:1–1.6:1 and about 30 ± 10% w/w acetals C and D.

These compositions are formed as follows:

Lotion: Emulsifiers, fatty alcohol and preservatives are combined with heating and stirring until homogeneous. To this homogeneous mixture is added the active with heating at about 50°-60° C. Water and thickener are then added with stirring and finally the perfume is added.

Aerosol: To the ethanol is added the isopropyl myristate with stirring. The active is then added, followed by the perfume to form a concentrate. Propellant is added in the requisite amount to the concentrate in an aerosol container.

As described above, the synergistic insect repellents of the invention have been found to be effective against flies and mosquitoes. It is to be expected that compositions of the invention will be effective against a variety of other insects including cockroaches, fleas, sandflies, mites, clothes moths and the like. In some cases additional insect repellent compounds may be required to achieve an appropriate level of repellency or the concentration of the synergistic insect repellent composition of the invention may need to be appropriately adjusted.

Whilst the present invention has been described with reference to certain preferred embodiments, it will be evident to those skilled in the art that numerous modifications and variations are possible without departing from the spirit or scope of the invention as broadly described.

We claim:

1. An insect-repellent composition comprising one or more insect repellents of the formula X:

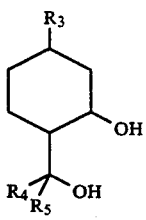

wherein R₃ is hydrogen or an alkyl group containing 1–4 carbon atoms; and R₄ and R₅ are the same or different and are alkyl groups containing 1–4 carbon atoms; and a synergistic amount of at least one compound of the formula Z:

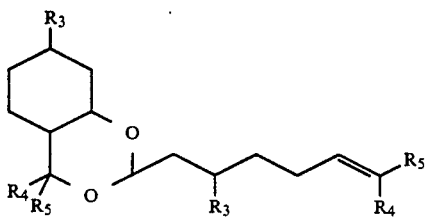

wherein R₃, R₄ and R₅ are as defined above, characterized in that the composition is substantially free of insect repellents having a boiling point of less than about 80° C. at a pressure of 4 mm Hg.

2. A composition as in claim 1, wherein the insect repellent is a compound of the formula X wherein R₃, R₄ and R₅ are methyl groups.

3. A composition as in claim 2, wherein the insect repellent comprises compounds of formula A and B:

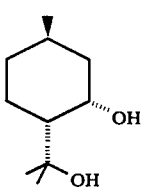

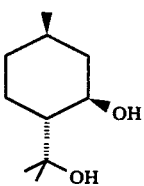

or the enantiomers thereof: and the compound of formula Z comprises diastereoisomers of the compound of formula E:

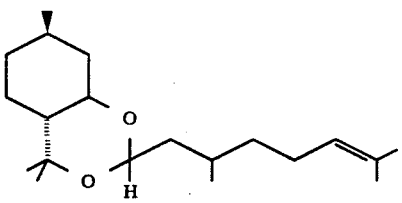

or the enantiomers thereof.

4. A composition as in claim 3, wherein the compound of formula E comprises two diastereoisomers of the compounds of formula C and D:

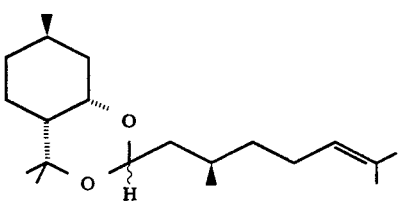

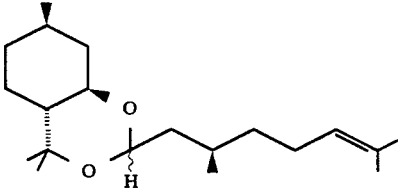

or the enantiomers thereof.

5. A composition as in any one of claim 4, wherein the weight ratio of insect repellent(s) to compound of the formula Z is from 99:1 to 1:99.

6. A composition as in claim 5, wherein the weight ratio is from 38:1 to 1:19.

7. A composition as in claim 6, wherein the weight ratio is from 19:1 to 1.6:1.

8. A composition as in claim 7, wherein the weight ratio is from 3.5:1 to 1.3:1.

9. A composition as in claim 8, including 20–40% w/w of the compounds C and D, and 57–63% w/w of a mixture of the compounds A and B.

10. A composition as in claim 9 formed by acid cyclizing citronellal and removing compounds having a boiling point less than about 80° C. at 4 mm Hg.

11. A composition as in claim 10, formed by acid cyclizing citronellal and removing compounds having a boiling point less than about 100° C. at 4 mm Hg.

12. An insect repellent in the form of an aerosol or lotion composition including about 5–50% w/w of a composition as claimed in claims 9, 10 or 11.

13. An insect repellent in the form of an aerosol or lotion composition as in claim 12 including about 30% w/w of said composition.

* * * * *

UNITED STATES PATENT AND TRADEMARK OFFICE
CERTIFICATE OF CORRECTION

PATENT NO. : 5,298,250
DATED : March 29, 1994
INVENTOR(S) : Brian D. Lett and Harold S. Kraus It is certified that error appears in the above-indentified patent and that said Letters Patent is hereby corrected as shown below:

Column 12, line 35: (Claim 5), delete --any one of--.

Signed and Sealed this

Second Day of May, 1995

Attest:

BRUCE LEHMAN

Attesting Officer    Commissioner of Patents and Trademarks